United States Patent [19]

Sjaunja et al.

[11] Patent Number: 5,343,044
[45] Date of Patent: Aug. 30, 1994

[54] INFRARED ATTENUATION MEASURING SYSTEM

[75] Inventors: Lars-Ove Sjaunja, Uppsala, Sweden; Steen K. Andersen, Hvidovre, Denmark; Börkur Arnvidarson, Niva, Denmark; Niels Brems, Virum, Denmark; Torben Lapp, Birkerod, Denmark; Lars Nygaard, Graested, Denmark

[73] Assignee: A/S Foss Electric, Hillerod, Denmark

[21] Appl. No.: 75,016

[22] Filed: Jun. 11, 1993

Related U.S. Application Data

[63] Continuation of Ser. No. 767,653, Sep. 30, 1991, abandoned.

[30] Foreign Application Priority Data

Sep. 27, 1991 [DK] Denmark .............................. 1653/91

[51] Int. Cl.$^5$ ...................... G01N 33/06; G01N 21/35
[52] U.S. Cl. ................................ 250/339.09; 250/343
[58] Field of Search ................. 250/343, 339, 340, 341

[56] References Cited

U.S. PATENT DOCUMENTS 3,161,768 12/1964 Goulden ............................... 250/339

(List continued on next page.)

FOREIGN PATENT DOCUMENTS 0122749 10/1984 European Pat. Off. ............. 250/339
57-14742 1/1982 Japan .................................. 250/339

OTHER PUBLICATIONS

Silver and Stanton, Optical Interference Fringe Reduction in Laser Absorption Experiments, Applied Optics, vol. 27, No. 10, pp. 1914-1916 May 15, 1988.

(List continued on next page.)

Primary Examiner—Paul M. Dzierzynski
Assistant Examiner—Drew A. Dunn
Attorney, Agent, or Firm—Birch, Stewart, Kolasch & Birch

[57] ABSTRACT

An infrared attenuation measuring system, for the quantitative determination of the concentration of one or more components in an aqueous fat-containing sample, such as milk, by an infrared attenuation technique. The system comprising a set of waveband-related parameters containing information enabling the system to calculate the concentrations substantially independent of the degree of homogenization of the fat-containing sample, and/or to determine the degree of homogenization of the sample. The parameter set contains parameters which are related to wavebands containing a high degree of information about the homogenization degree of the sample. This may be wavebands containing little information about the chemical components of the sample, and/or wavebands containing a substantial amount of information about the chemical components of the sample. The system is calibrated with aqueous fat-containing samples with different degrees of homogenization. The calculating means may be a microprocessor calculating the concentration of the component or components in question, or a neural network defined by the wave band-related parameters. The wavebands in which the attenuation values are determined in the infrared attenuation measuring means may be defined by optical filters, stationary grating and movable and-/or multiple detectors, or by movable grating and one or several stationary or movable detectors. The infrared attenuation measuring means may comprise an interferometer, the data obtained from the interferometer being processed using Fourier transformation; and infrared attenuation measuring means of this type may be a FTIR spectrophotometer.

42 Claims, 3 Drawing Sheets

U.S. PATENT DOCUMENTS

| | | | |
|---|---|---|---|
| 4,076,983 | 2/1978 | Hopkins et al. | 250/343 |
| 4,207,469 | 6/1980 | Hopkins et al. | 250/343 |
| 4,247,773 | 1/1981 | Nexo et al. | 250/339 |
| 4,310,763 | 1/1982 | Shields | 250/339 |
| 4,415,809 | 11/1983 | Shields | 250/432 |
| 4,447,725 | 5/1984 | Biggs et al. | 250/343 |
| 4,663,530 | 5/1987 | Shields | 250/343 |
| 4,730,112 | 3/1988 | Wong | 250/343 |
| 4,746,218 | 5/1988 | Lord, III | 250/343 |
| 4,749,276 | 6/1988 | Bragg et al. | 250/343 |
| 4,849,637 | 7/1989 | Cerff et al. | 250/343 |
| 4,883,963 | 11/1989 | Kemeny et al. | 250/343 |
| 4,897,548 | 1/1990 | Dome et al. | 250/343 |
| 4,934,816 | 6/1990 | Silver et al. | 250/343 |
| 4,937,448 | 6/1990 | Mantz et al. | 250/343 |

OTHER PUBLICATIONS

Gehrtz and Bjorklund, Quantum-Limited Laser Frequency-Modulation Spectroscopy, J. Opt. Soc. Am. B, vol. 2, No. 9, pp. 1510–1526, Sep. 1985.

Carlisle, Cooper and Preier, Quantum Noise-Limited FM Spectroscopy with a Lead-Salt Diode Laser, Applied Optics, vol. 28, No. 13, pp. 2567–2576, Jul. 1, 1989.

J. Reid, M. El-Sherbiny, B. K. Garside, and E. A. Ballik, Applied Optics Sensitivity Limits of a Tunable Diode Laser Spectrometer, with Application to the Detection of $NO_2$ at the 100-ppt Level, pp. 3349–3354.

D. T. Cassidy and J. Reid, Applied Physics B, Harmonic Detection with Tunable Diode Lasers–Two-Tone Modulation, pp. 279–285, 1982.

INFRARED ATTENUATION MEASURING SYSTEM

This application is a continuation of application Ser. No. 07/767,653 filed on Sep. 30, 1991, now abandoned.

The present invention relates to an infrared attenuation measuring system for the quantitative determination of the concentration of one or more components in an aqueous fat-containing sample by an infrared attenuation technique.

It is known to determine the fat content in fat-containing samples, in particular milk samples, by infrared attenuation techniques. In the present context, the term "infrared attenuation technique" is intended to designate a measuring technique where light in the infrared range is transmitted to a sample, and the attenuation of the infrared light (which may be due to light scattering or energy absorption) caused by the sample is measured.

Systems, or instruments, for the measurement comprise infrared attenuation measuring means for measuring the infrared attenuation of the sample in a number of wavebands and calculating means which are adapted to calculate the concentrations of the components of the fat-containing sample based on the measured infrared attenuation values of the sample. The calculation is performed using a set of waveband-related parameters which have normally been established by a factory calibration of the system or instrument.

One problem associated with such infrared measurement on, e.g., milk samples, is that the calculated results (often called predicted results, because the "real" analysis results are results obtained using the standard chemical reference methods) vary with varying fat globule size distribution in the samples. All the known instruments or systems used for the measurements are adapted to measure, in their cuvettes, on homogenized samples and contain built-in homogenizers which are supposed to ensure that the various milk samples subjected to measurement have been subject to identical homogenization so that they have identical fat globule size distribution. However, the homogenizers of the systems of instruments are subject to mechanical wear, which means that their homogenizing efficiency decreases with time, thereby resulting in variations in the fat globule size distributions and thus to less accurate measurements.

In connection with research where the built-in homogenizer of infrared attenuation measuring systems was bypassed, and the calibration of the systems was performed with systematic inclusion of samples with different fat globule size distributions, it was surprisingly found, based upon systematic and thorough investigation, that it is possible to obtain information on the fat globule size distribution from the infrared attenuation spectrum. It was also found that suitable calibration and processing of the calibration data made it possible to include, in the parameter set resulting from the calibration, information enabling the calculating means of the systems or instruments to either ensure that the calculated concentrations are substantially independent on the degree of homogenization of the fat-containing sample, and/or to determine the degree of homogenization of the sample, the latter determination being particularly useful in assessing the efficiency of the built-in homogenizer of the systems/instruments.

These findings give rise to a considerable improvement of the reliability and working life of the systems, and/or to the possibility of making very simple and cheap systems without built-in homogenizer, but still permitting a remarkably high accuracy in the measured results.

In the present context, the term "degree of homogenization" is intended to indicate the mean diameter, calculated by volume, of the fat globules. It is well known that with increasing homogenization efficiency (increasing degree of homogenization), the mean diameter of the fat globules will decrease, which, on the other hand, means that with decreasing homogenization efficiency (decreasing degree of homogenization), there will be an increase in the mean diameter of the fat globules size, which will cause increased light scattering the thus decrease the accuracy of the measurements of the known art instruments. In practice, the variation around the mean fat globule size will also tend to decrease with decreasing mean diameter (increasing degree of homogenization). In the present context, the term "degree of homogenization" is used in a broad sense and is thus also used to characterize the fat globule size of unhomogenized natural samples (which of course have a low degree of homogenization); the measurement, on samples having a low degree of homogenization, corresponding to the samples being natural unhomogenized samples, with highly reliable results is a fascinating possibility opened up by the present invention.

Based on the discoveries of the present invention, it now becomes possible not only to determine the degree of homogenization of the samples on which the measurements are made, the determination being made as part of the normal measurement, but also to retain the accuracy which previously required, a built-in homogenizer of top performance by using the information derivable from the spectrum, associated with suitable calibration principles, for automatically compensating for differences in degree of homogenization.

The determination of the degree of homogenization can suitably be made by defining a value ascribed to a calibration sample of known fat globule size distribution and calculating, in connection with the measurement on a particular sample, the corresponding value in relation to the sample of the known fat globule size distribution. This determination can be performed in the presence of varying concentrations of the components of the sample, see Example 2.

The compensation resulting in virtual independence of the performance of the built-in homogenizer of the system is suitably obtained by using data from calibrations to establish parameter sets which, when used in connection with the measured attenuations, will result in predicted values in which deviations in the degree of homogenization are compensated for.

The parameter set normally contains parameters which are related to wavebands containing a high degree of information about the homogenization degree of the sample. This may be wavebands containing little information about the chemical components of the sample, and/or wavebands containing a substantial amount of information about the chemical components of the sample. As explained in the following and illustrated in the examples, certain mathematical methods are extremely useful for establishing, based on suitable calibration data, a parameter set which will be especially suitable for the purpose of the invention.

BRIEF DESCRIPTION OF THE DRAWINGS

FIG. 2 shows infrared transmission spectra of three aqueous fat-containing samples A, B and C. Samples A and B correspond to samples A and B, respectively, in FIG. 1, and sample C is sample B following homogenization through a 2-stage ball valve homogenizer with a total pressure drop of 100 bar, the pressure drop of each stage being 50 bar. The fat globules of sample C had a mean diameter of volume ($d_{volume}$) of 1.9 $\mu$m with 1% of the fat globules having a diameter larger than 4 $\mu$m.

FIG. 3 shows a bar diagram as described in Example 2. The solid bars are the results of the entire data set obtained whereas the open bars are the results from test set models.

DETAILED DESCRIPTION OF THE INVENTION

In one aspect the present invention relates to an infrared attenuation measuring system for the quantitative determination of the concentration of one or more components in an aqueous fat-containing sample by an infrared attenuation technique, the system comprising infrared attenuation measuring means for measuring the infrared attenuation of the sample in a number of wavebands and calculating means which are adapted to calculate the concentrations of the components of the fat-containing sample from the measured infrared attenuation values of the sample using a set of waveband-related parameters, the parameter set containing information enabling the calculating means to ensure that the calculated concentrations are substantially independent on the degree of homogenization of the fat-containing sample, and/or to determine the degree of homogenization of the sample.

In the present context, the term "system" designates any system capable of performing the measurement and the calculation, irrespective of whether the system is integrated in one instrument or consists of several units such as a measuring unit and a separate calculating unit such as a microcomputer.

The parameter set mentioned above contains parameters which are related to wavebands containing a high degree of information about the homogenization degree of the sample.

In the present specification with claims, the term "waveband" is intended to mean a wavenumber range in the infrared spectrum. The width of a waveband will be selected in dependency of the system used, the information in the spectrum, etc. One example of a waveband width if the 20 cm$^{-1}$ used in the examples, but waveband widths useful for the purpose of the present invention may vary over broad range, such as up to 100 cm$^{-1}$, depending, i.a., on the location in the spectrum, such as whether in the long wave or the short wave end of the spectrum.

The calculating means may, e.g., be a microprocessor calculating the concentrations using, e.g. a linear combination of attenuation values and/or functions of attenuation values, the wave band-related parameters being coefficients in the linear combination. The parameters may be stored in the system in any suitable storage, such as a hard disc, a ROM, a RAM, a PROM, a CD, a chip, a tape, etc. As an interesting contemplated alternative, the calculating means may be a neural network defined by the wave band-related parameters. In one embodiment, the results of the linear combination are further processed in the neural network.

The waveband-related parameters are not values directly corresponding to physical or chemical properties, but are rather parameters determined empirically and/or statistically in the calibration of the system.

The parameters are waveband-related, that is, the parameters are used by the calculating means when treating the measured attenuation values in the waveband in question, and are determined as a result of the calibration of the system on the basis of values from the waveband in question.

The parameter set may contain parameters which are related to wavebands containing a high degree of information about the homogenization degree of the sample. The wavebands containing a high degree of information about the homogenization degree of the sample comprise wavebands containing little information about the chemical components of the sample, and/or wavebands containing a substantial amount of information about the chemical components of the sample. In connection with the discussion of FIGS. 1 and 2 below, such types of wavebands containing a high degree of information about the degree of homogenization are discussed.

Normally, the parameter set will contain information related to wavebands over a relatively broad range, including, e.g. a parameter related to wavebands about 3400 cm$^{-1}$, parameter related to a waveband in the range between 3400 cm$^{-1}$ and 4000 cm$^{-1}$, a parameter related to wavebands in the range of 2600–3400 cm$^{-1}$, a parameter related to wavebands in the range of 2700–3100 cm$^{-1}$, a parameter related to wavebands in the range of 2000–2600 cm$^{-1}$, a parameter related to wavebands in the range of 800–2000 cm$^{-1}$, a parameter related to wavebands in the range of 900–1700 cm$^{-1}$, a parameter related to wavebands in the range of 1000–1600 cm$^{-1}$, and/or a parameter related to wavebands in the range of 1600–1800 cm$^{-1}$.

The attenuation values may be determined in wavebands defined by optical filters, or they may be determined in wavebands defined by stationary grating and movable and/or multiple detectors, or by movable grating and one or several stationary or movable detectors.

In important embodiments of the system according to the invention, the attenuation values are determined over a broad spectrum range using an interferometer, and the data obtained from the interferometer are processed using Fourier transformation. An example of such as system if illustrated in Examples 1 and 2.

The crucial parameters used according to the invention are normally established by calibration of the system with aqueous fat-containing samples with different homogenization degrees. The systematic calibration of the system with samples with different homogenization degrees is believed to be a completely novel concept utilizing the finding that in this manner, information latently present in the spectrum can be rendered available for the important establishment of measurements substantially free from influence from the homogenization degree, or for the monitoring of the quality of a homogenizer, such as a homogenizer built into a measuring system of the present type.

In an interesting embodiment, an infrared attenuation measuring system according to the invention may comprise a built-in homogenizer which is by-passable so as to permit calibration with pre-prepared aqueous fat-containing samples with different homogenization degrees, or the homogenizer, alternatively, may be adjustable to deliver different levels of homogenization useful for such calibration.

Normally, however, the calibration according to the invention (see below) to establish the system according to the invention is performed at the factory only once in the lifetime of the system, with the possibility of validation upon replacement of vital parts of the system.

Expressed by means of its capability of predicting exactly on samples of different degrees of homogenization, a system according to the invention may be characterized as an infrared attenuation measuring system which, when measuring fat on an unhomogenized raw milk sample containing 2-4% of fat and a sample of the same raw milk homogenized to a mean fat globule diameter of volume of 1 $\mu$m, respectively, measures fat contents which show a relative deviation from each other of at the most 4%, preferably at the most 3%, and more preferably at the most 2%.

The invention also relates to a method for the establishment of a system as described above, the method comprising subjecting an infrared attenuation measuring system for the quantitative determination of the concentration of one or more components in an aqueous fat-containing sample by an infrared attenuation technique, the system comprising infrared attenuation measuring means for measuring the infrared attenuation of the sample in a number of wavebands and calculating means which are adapted to calculate the concentrations of the components of the fat-containing sample from the measured infrared attenuation values of the sample using a set of waveband-related parameters, to calibration with aqueous fat-containing samples with different degrees of homogenization to establish a calibration parameter set containing information enabling the calculating means to ensure that the calculated concentrations are substantially independent on the degree of homogenization of the fat-containing sample, and/or to determine the degree of homogenization of the sample.

The calibration may be performed by measuring, at different wavebands including, at least, for each component to be measured, a waveband at which the component in question influences the infrared attenuation, and a waveband at which the attenuation has a relatively high dependency on the degree of homogenization, and a relatively low dependency on the concentration of the individual components, attenuation on either 1) a set of samples each of which, for each component to be measured, contains a known concentration of the component, at least two of the samples containing fat of different degrees of homogenization, or 2) at least two samples containing the same concentration of fat, but of different degrees of homogenization, the system having, in advance, being calibrated with respect to the chemical components to be measured, and, on the basis of the resulting data sets, establishing a calibration parameter set containing information enabling the calculating means to ensure that the calculated concentrations are substantially independent on the degree of homogenization of the fat-containing sample, and/or to determine the degree of homogenization of the sample.

The establishment of the calibration parameter set is advantageously performed using a partial least square algorithm, or it may be performed using a principal component regression algorithm, such as by a multiple linear regression.

The number of samples used in the calibration normally corresponds to at least the number of wavebands, and the results of the measurements are normally arranged in a set of linear equations which are solved by matrix algebra to calculate the parameters. In most cases, a larger number of samples is used, depending on the number of components to be estimated and their respective interaction. The quality of the calibration will normally be checked using a test set which has been kept out of the calibration set to ensure the stability of the system with respect to random variables.

The samples to be measured are often milk samples, and the components to be determined are often selected from the group consisting of fat, protein, lactose, other carbohydrates, citric acid, urea, free fatty acids, antibiotics, somatic cells, and casein. In addition to milk samples, "milk-like" samples, such as samples prepared from cheese, butter, and other milk products are prominent sample types which can be measured in the system according to the invention.

Figure 1:
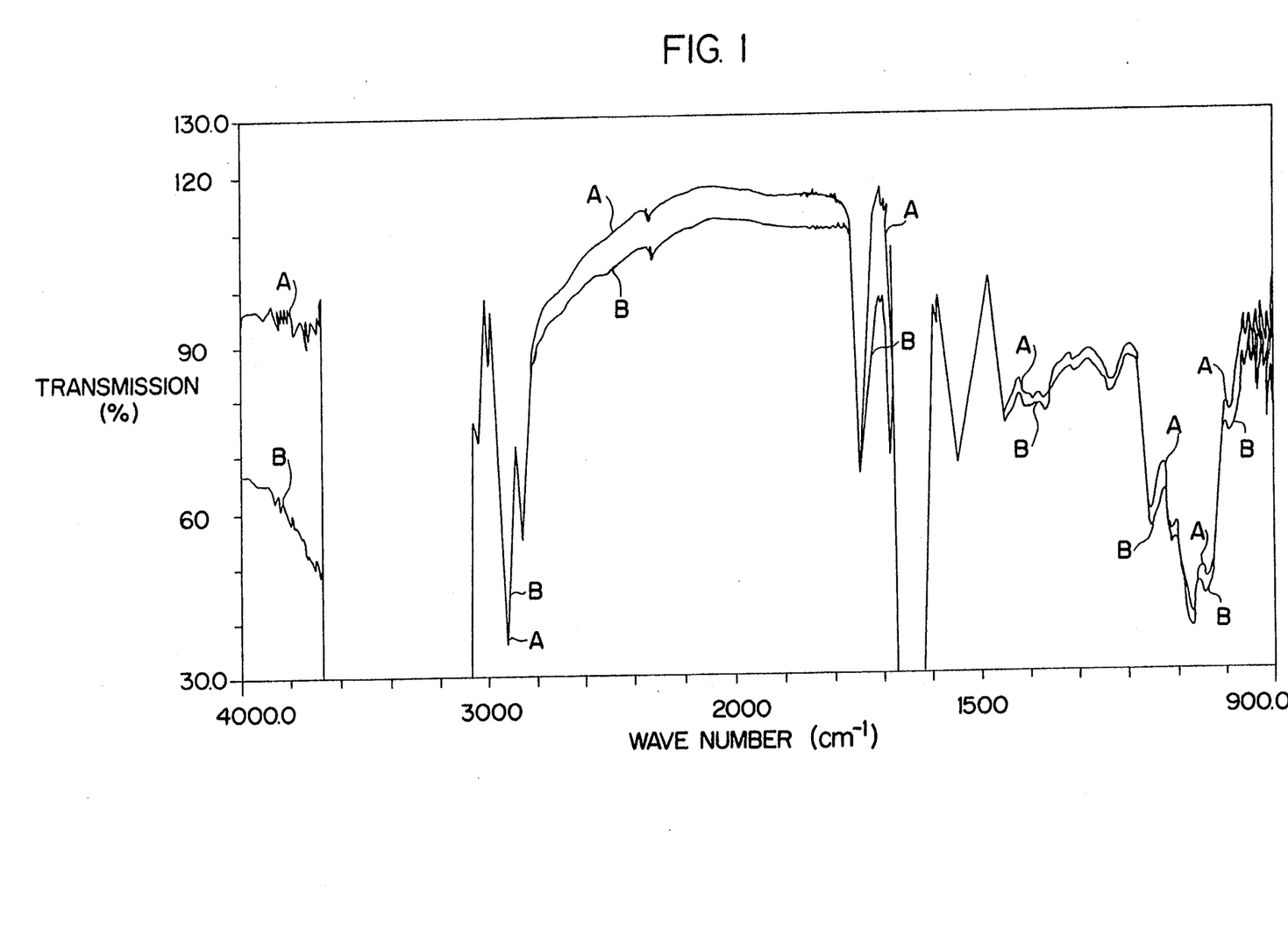
FIG. 1 shows infrared transmission spectra of two milk samples A and B, sample A containing approximately 3% fat and the fat globules having a mean diameter of volume ($d_{volume}$) of 0.9 $\mu$m with 1% of the fat globules having a diameter larger than 2.5 $\mu$m, and sample B being the unhomogenized equivalent of sample A and the fat globules having a mean diameter of volume of 4 $\mu$m with 1% of the fat having a globule diameter larger than 12 $\mu$m. Sample A was obtained by homogenizing sample B through a 2-stage ball valve homogenizer with a total pressure drop of 200 bar, the pressure drop of each stage being 100 bar.

From FIG. 1 it is seen that the infrared transmission spectra of the two samples having different degrees of homogenization, one sample having a relatively high degree of homogenization and the other being unhomogenized, differ almost over the whole range of wavenumbers. These findings indicate that the contribution of the degree of homogenization of an aqueous fat-containing sample may be calculated over a broad range of wavenumbers. Most important, however, is the finding that the main difference in the transmission spectra is seen for wavenumbers about approximately 3700 cm$^{-1}$. Thus, the largest difference in the spectra of the two different sample is obtained by measuring the infrared transmission at a wavenumber in this region giving rise to the assumption that measurement above 3700 cm$^{-1}$ followed by proper calculations could establish a parameter for use in determining the degree of homogenization. Furthermore, in connection with measurement of infrared transmission of an aqueous fat-containing sample in order to determine the concentration of one or more components like fat, protein, lactose, citric acid, urea or the like in an aqueous fat-containing sample, information collected at a wavenumber about 3700 cm$^{-1}$ seems to be useful in order to establish a parameter for use in determination of the concentration of one or more components in the sample taken the degree of homogenization of the sample into account.

Figure 2:
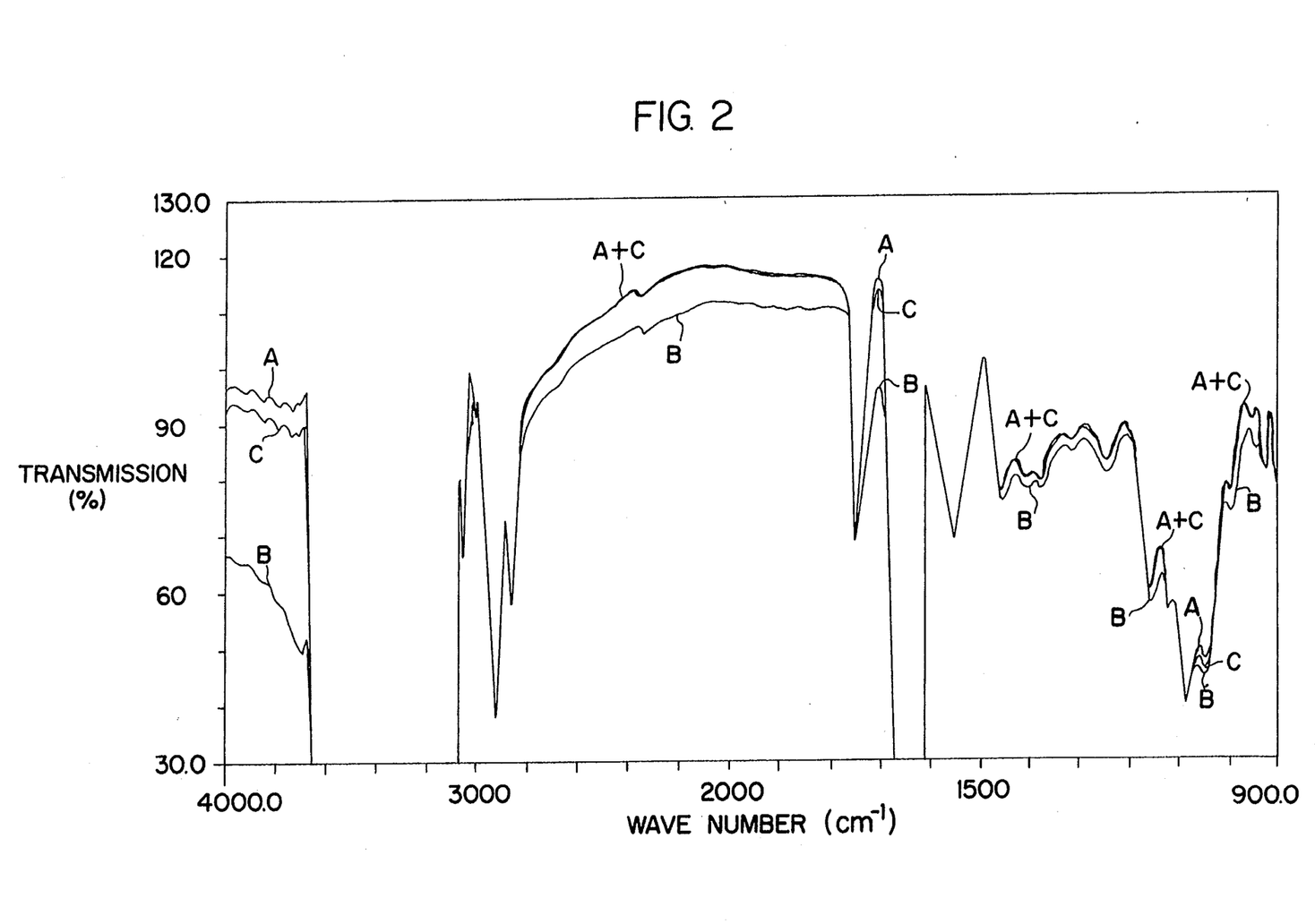

In FIG. 2 is shown infrared transmission spectra from three sample having different degrees of homogenization as described above. Like in FIG. 1, the influence of the degree of homogenization is most evident for measurements performed at wavenumbers above about 3700 cm$^{-1}$ and the curve relating to sample C is found to be placed between the curves of the two other samples, thus, indicating that a relationship between measurements at such wavenumbers and the degree of homogenization is present.

Figure 3:
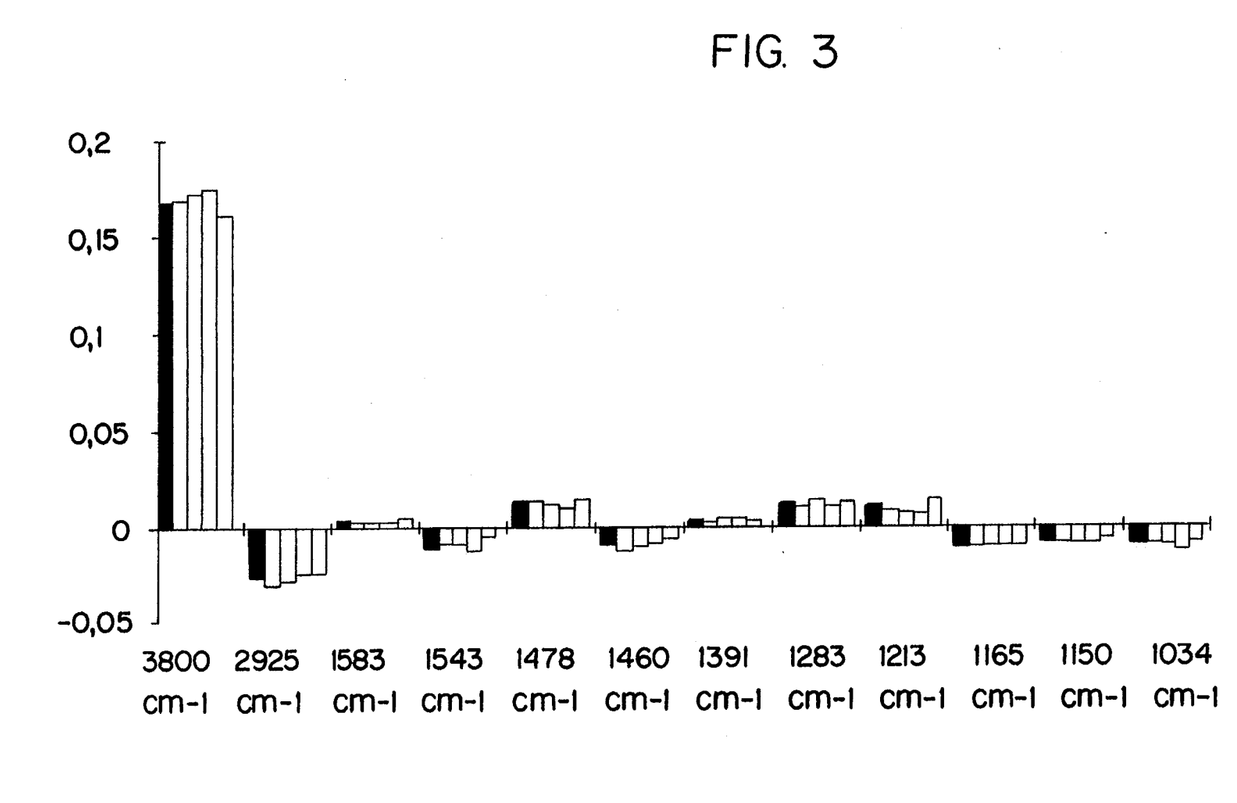

With regard to detailed description of FIG. 3, reference is made to the description in Example 2 below.

The invention is further illustrated by the following non-limiting examples.

EXAMPLE 1

Calibration of an Infrared Attenuation Measuring System Using a Sample Set with Two Different Degrees of Homogenization and a Sample Set with One Degree of Homogenization and Determination of Individual Component Concentrations on Samples of the Sample Sets The sample material was prepared from a starting sample collection consisting of 40 raw milk samples, 10 of which were herd samples (i.e. mixtures of the milk from an entire cow herd) and the rest were obtained from individual cows, the purpose being to provide a sufficient variation in the contents of the major milk components (fat, protein, lactose).

Portions of each of the 40 samples were analyzed by reference methods for the determination of fat, protein and lactose, the methods being Röse-Gottlieb, Kjeldahl, and Luff-Schoorl, respectively.

Three portions of each sample were homogenized, one at 100 bar, the other two at 200 bar, in a two-stage ball valve homogenizer, the individual pressure drops in each homogenizer being 50 plus 50 bar, and 100 plus 100 bar, respectively. The pump used to run the homogenizer was a Foss Electric standard rotary-piston high pressure pump. The homogenized sample portions constituted the sample sets for calibration as follows: One sample set (A), for the calibration according to the invention, consisted of 40 portions homogenized at 100 bar and 40 portions homogenized at 200 bar. The other sample set (B), for a reference calibration, consisted of 40 portions homogenized at 200 bar.

In order to characterize the two homogenizers, a single sample from the original collection of unhomogenized samples, as well as the corresponding samples homogenized at 100 and 200 bar, respectively, were subjected to fat globule size distribution analysis. The unhomogenizer sample had a mean diameter of volume ($d_{volume}$) of 4 $\mu$m with 1% of the fat having a globule diameter larger than 12 $\mu$m. The sample homogenized at 100 bar had a $d_{volume}$ of 1.9 $\mu$m with 1% of the fat globules having a diameter larger than 4 $\mu$m, whereas the sample homogenized at 200 bar had a $d_{volume}$ of 0.9 $\mu$m with 1% of the fat globules having a diameter larger than 2.5 $\mu$m.

In the measuring compartment of a Perkin-Elmer 1710 Fourier Transform Infra-red spectrophotometer controlled by a IBM-PC-compatible personal computer running a Perkin-Elmer IR-DataManager software, two identical interchangeable (sample shuttle) cuvettes with calcium fluoride windows and a light path of 37 $\mu$m were inserted, one of which was filled with deionized water, and the other being filled with the relevant milk sample. The sample cuvette was connected directly to the above described homogenizer and pump system. Each cuvette was further thermostated at 40° C.

Calibration According to the Invention

The 2×40 samples (A) homogenized at 100 and 200 bar, respectively, were injected into the sample cuvette, and a full range spectrum (4000–900 cm$^{-1}$) was recorded, the resolution selected being 2 cm$^{-1}$ giving a total of 3101 data points. The spectra were collected in digitized form for later numerical analysis. 24 hours after the recordal of the first 80 spectra, another series of spectra of the 40 (A) samples homogenized at 200 bar were recorded. Thus, the total number of digitized spectra were 120.

In order to reduce the amount of data to be analyzed, 12 absorbance values defined as the mean absorbance in a 20 cm$^{-1}$ window centered around the following wave numbers were calculated from each of the digitized spectra: 3800, 2925, 1583, 1543, 1478, 1460, 1391, 1283, 1213, 1165, 1155, and 1034 cm$^{-1}$.

The resulting 120 sets of twelve absorbance values and the corresponding standard analysis results for the 40 samples were subjected to Partial Least Square analysis (as described, e.g., in "Multivariate Calibration" by Harald Martens and Tormod Naes, John Wiley & Sons, London, 1989, pp 116–125), thereby calibrating the system resulting in a set of regression equations characteristic to the calibrated system.

The set of regression equations for each component (fat, protein, lactose) consisted of a set of terms comprising a regression coefficient (B-coefficient) and the corresponding absorbance value at each of the 12 spectral windows listed above and a constant term. In the table below, the regression coefficients and constant terms are listed.

| Spectral Window | B-coefficient | | |
|---|---|---|---|
| | Fat | Protein | Lactose |
| 3800 cm$^{-1}$ | 3.3046 | .1886 | −.5000 |
| 2925 cm$^{-1}$ | 10.9571 | 2.0270 | .6475 |
| 1583 cm$^{-1}$ | −2.1820 | 1.7892 | −14.5792 |
| 1543 cm$^{-1}$ | −1.7250 | 16.9867 | −4.9432 |
| 1478 cm$^{-1}$ | −1.2840 | −1.1404 | 6.2963 |
| 1460 cm$^{-1}$ | .6523 | 4.2474 | 7.2961 |
| 1391 cm$^{-1}$ | −.8554 | −12.2288 | 26.6697 |
| 1283 cm$^{-1}$ | −.3156 | −1.8824 | −.8149 |
| 1213 cm$^{-1}$ | .0854 | 2.7227 | 5.2450 |
| 1165 cm$^{-1}$ | 2.4827 | −.2974 | −20.3297 |
| 1155 cm$^{-1}$ | 2.0327 | 1.1259 | 9.6517 |
| 1034 cm$^{-1}$ | −2.4676 | 1.1120 | 7.5539 |
| Constant | −.7444 | .5296 | .7499 |

In this calibration, the standard analysis results were determined (predicted) using all 120 sets of absorbance values. The result was that the number of factors suggested by cross validation was 4 for the estimation of fat, 6 for the estimation of protein, and 7 for the estimation of lactose.

Determination of quality (predictability) of the system according to the invention: The standard errors of prediction resulting from the above calibration were 1.4% of mean value for fat, 1.1% for protein, and 2.2% for lactose.

Reference calibration: The same procedure as explained above was repeated using the sample set (B) homogenized at 200 bar. The result was that the number of factors suggested by cross validation was 2 for the estimation of fat, 5 for the estimation of protein, and 6 for the estimation of lactose.

Reference determination: The standard errors of prediction resulting from the reference calibration were 1.5% of mean value for fat, 1.1% for protein, and 2.2% for lactose.

CONCLUSION

The above results demonstrate that it was possible to obtain the same low error of prediction when predicting, in the system according to the invention (calibrated by the method according to the invention) samples of different degree of homogenization as when predicting samples of identical degree of homogenization in the system which was not calibrated with systematic use of samples of different degree of homogenization. The only difference was that the prediction model for the system according to the invention was of a higher complexity as illustrated by the higher number of factors needed compared with the data set representing samples of identical degree of homogenization. The stability of the system according to the invention was demonstrated by subdividing all the samples ((A) and (B) together) into 4 groups at random and then in turn establishing a calibration model based on the data from three of the sample groups and using the fourth group as a test group calculating the standard error of prediction. In each of the four such possible stability tests, the standard errors of prediction obtained did not differ significantly from those obtained in the first and second predictive models described above. This shows that the system according to the invention is stable.

EXAMPLE 2

The same absorbance value data obtained in Example 1 was analyzed with regard to the ability of the data from the individual spectral windows to predict whether the individual sample had been homogenized at 100 or at 200 bar. This was down by assigning to each sample an arbitrary homogenization index (0 for 200 bar and 1 for 100 bar) and subjecting the absorbance values and homogenization indexes to Partial Least Square Analysis.

The model was able to assign all samples correctly. The resulting B-coefficients using 3 factors as suggested from cross validation are shown on FIG. 3. The solid bars are the results of the entire set of data whereas the open bars are the results from test set models calculated in the same manner as in Example 1, i.e. by generating a model using three quarters of the data and testing the model on the remaining quarter of the data. The results on FIG. 3 firstly show that the model was stable in that the open bars are of the same size and, secondly, that the major response to variations in homogenization efficiency is found in the spectral window at around 3800 $cm^{-1}$.

These results show that it is possible to establish, based upon information about degree of homogenization along, a system according to the invention which is able to predict a parameter related to the degree of homogenization in samples containing varying amounts of milk components. This system is useful for monitoring the efficiency of a homogenizer built into an instrument or system for infrared attenuation measurement on aqueous fat-containing samples.

We claim:

1. A method for the quantitative determination of the concentration of one or more components in an aqueous fat-containing sample by an infrared attenuation measuring technique, the method comprising measuring the infrared attenuation of a sample in one or more wavebands and calculating the concentrations of the components of the fat-containing sample from the measured infrared attenuation values of the sample using a set of waveband-related parameters, the parameter set containing information ensuring that the calculated concentrations are substantially independent of the degree of homogenization of the fat-containing sample, said information being derived from a calibration with aqueous fat-containing samples having different degrees of homogenization.

2. A method according to claim 1, wherein the parameter set has been established by a calibration performed by measuring, at different wavebands including, at least, for each component to be measured, a waveband at which the component in question influences the infrared attenuation, and a waveband at which the attenuation has a relatively high dependency on the degree of homogenization, and a relatively low dependency on the concentration of the individual components, attenuation on either
   1) a set of samples each of which, for each component to be measured, contains a known concentration of the component, at least two of the samples containing fat of different degrees of homogenization, or
   2) at least two samples containing the same concentration of fat, but of different degrees of homogenization, a calibration having, in advance, been performed with respect to the chemical components to be measured.

3. A method according to claim 1, in which the parameter set contains parameters which are related to wavebands containing a high degree of information about the homogenization degree of the sample.

4. A method according to claim 3, wherein the wavebands containing a high degree of information about the homogenization degree of the sample comprise wavebands containing little information about the chemical components of the sample, and/or wavebands containing a substantial amount of information about the chemical components of the sample.

5. A method according to claim 1, in which the parameter set contains a parameter related to wavebands above 3400 $cm^{-1}$.

6. A method according to claim 5, wherein the parameter related to wavebands above 3400 $cm^{-1}$ is a parameter related to a waveband in the range between 3400 $cm^{-1}$ and 4000 $cm^{-1}$.

7. A method according to claim 1, in which the parameter set contains a parameter related to wavebands in the range of 2600-3400 $cm^{-1}$.

8. A method according to claim 7, in which the parameter set contains a parameter related to wavebands in the range of 2700-3100 $cm^{-1}$.

9. A method according to claim 1, in which the parameter set contains a parameter related to wavebands in the range of 2000-2600 $cm^{-1}$.

10. A method according to claim 1, in which the parameter set contains a parameter related to wavebands in the range of 800-2000 $cm^{-1}$.

11. A method according to claim 10, in which the parameter set contains a parameter related to wavebands in the range of 900-1700 $cm^{-1}$.

12. A method according to claim 10, in which the parameter set contains a parameter related to wavebands in the range of 1000-1600 $cm^{-1}$.

13. A method according to claim 10, in which the parameter set contains a parameter related to wavebands in the range of 1600-1800 $cm^{-1}$.

14. A method according to claim 1, wherein the concentrations are calculated using a linear combination of attenuation values and/or functions of attenuation values, the parameters being coefficients in the linear combination.

15. A method according to claim 1, wherein the accuracy is such that a comparison of the measured fat content of an unhomogenized raw milk sample containing 2-4% of fat with the measured fat content of a sample of the same raw milk homogenized to a mean fat globule diameter of volume of 1 μm, shows a relative deviation of at the most 4%.

16. A method according to claim 1, wherein the accuracy is such that a comparison of the measured fat content of an unhomogenized raw milk sample containing 2-4% of fat with the measured fat content of a sample of the same raw milk homogenized at a mean fat globule diameter of volume of 1 μm, shows a relative deviation of at the most 3%.

17. A method according to claim 1, wherein the accuracy is such that a comparison of the measured fat content of an unhomogenized raw milk sample containing 2-4% of fat with the measured fat content of a sample of the same raw milk homogenized at a mean fat globule diameter of volume of 1 μm, shows a relative deviation of at the most 2%.

18. A method according to claim 1, wherein the sample to be measured is a milk sample, and the components to be determined are selected from the group consisting of fat, protein, carbohydrates, citric acid, urea, free fatty acids, antibiotics, somatic cells, and casein.

19. A method according to claim 18, wherein the component to be determined is lactose.

20. A method according to claim 1, wherein no homogenization of the sample is performed.

21. A method for the quantitative determination of the concentration of one or more components in an aqueous fat-containing sample by an infrared attenuation measuring technique, the method comprising measuring the infrared attenuation of a sample in one or more wavebands and calculating the concentrations of the components of the fat-containing sample from the measured infrared attenuation values of the sample using a set of waveband-related parameters, the parameter set containing information ensuring that the calculated concentrations are substantially independent of the degree of homogenization of the fat-containing sample, so that a comparison between the measured fat content of an unhomogenized raw milk sample containing 2-4% of fat with the measured fat content of a sample of the same raw milk homogenized to a mean fat globule diameter of volume of 1 μm, shows a relative deviation of at the most 4%.

22. A method according to claim 21, wherein the relative deviation is at the most 3%.

23. A method according to claim 21, wherein the relative deviation is at the most 2%.

24. A method for the quantitative determination of the concentration of one or more components in an aqueous fat-containing sample by an infrared attenuation measuring technique, the method comprising measuring the infrared attenuation of a sample in one or more wavebands and calculating the concentrations of the components of the fat-containing sample from the measured infrared attenuation values of the sample using a set of waveband-related parameters, the parameters containing information being derived from a calibration with aqueous fat-containing samples having different degrees of homogenization.

25. A method for the calibration of an infrared attenuation measuring system for the quantitative determination of the concentration of one or more components in an aqueous fat-containing sample by an infrared attenuation measuring technique, the system calculating the concentrations of the components of the fat-containing sample from measured infrared attenuation values of the sample using a set of waveband-related parameters, the method comprising establishing the parameter set by calibrating the system with aqueous fat-containing samples with different degrees of homogenization.

26. A method according to claim 25, wherein the calibration is performed by measuring, at different wavebands including, at least, for each component to be measured, a waveband at which the component in question influences the infrared attenuation, and a waveband at which the attenuation has a relatively high dependency on the concentration of the individual components, attenuation on either 1) a set a samples each of which, for each component to be measured, contains known a known concentrations of the component, at least two of the samples containing fat of different degrees of homogenization, or
2) at least two samples containing the same concentration of fat, but of different degrees of homogenization, the system having, in advance, being calibrated with respect to the chemical components to be measured, and, on the basis of the resulting data sets, establishing a calibration parameter set.

27. A method according to claim 25, wherein the establishment of the set of waveband-related parameters is performed using a partial least square algorithm.

28. A method according to claim 27, wherein the establishment of the partial least square algorithm is performed using a multiple linear regression.

29. A method according to claim 25, wherein the establishment of the set of waveband-related parameters is performed using a principal component regression algorithm.

30. A method according to claim 25, wherein the number of samples corresponds to the number of wavebands, and the results of the measurements are arranged in a set of linear equations which are solved by matrix algebra to calculate the parameters.

31. A method for the determination of the degree of homogenization of an aqueous fat-containing sample by an infrared attenuation measuring technique, the method comprising measuring the infrared attenuation of the sample in one or more wavebands and calculating the degree of homogenization of the fat-containing sample from the measured infrared attenuation values of the sample using a set of waveband-related parameters containing information being derived from a calibration with aqueous fat-containing samples having different degrees of homogenization.

32. A method according to claim 31, wherein the parameter set contains parameters which are related to wavebands containing a high degree of information about the homogenization degree of the sample.

33. A method according to claim 31, wherein the parameter set contains a parameter related to wavebands above 3400 cm$^{-1}$.

34. A method according to claim 33, wherein the parameter related to wavebands above 3400 cm$^{-1}$ is a parameter related to a waveband in the range between 3400 cm$^{-1}$ and 4000 cm$^{-1}$.

35. A method according to claim 1, wherein the parameter set contains a parameter related to wavebands in the range of 2600-3400 cm$^{-1}$.

36. A method according to claim 35, wherein the parameter set contains a parameter related to wavebands in the range of 2700-3100 cm$^{-1}$.

37. A method according to claim 31, wherein the parameter set contains a parameter related to wavebands in the range of 2000–2600 cm$^{-1}$.

38. A method according to claim 31, wherein the parameter set contains a parameter related to wavebands in the range of 800–2000 cm$^{-1}$.

39. A method according to claim 38, wherein the parameter set contains a parameter related to wavebands in the range of 900–1700 cm$^{-1}$.

40. A method according to claim 38, wherein the parameter set contains a parameter related to wavebands in the range of 1000–1600 cm$^{-1}$.

41. A method according to claim 38, wherein the parameter set contains a parameter related to wavebands in the range of 1600–1800 cm$^{-1}$.

42. A method according to claim 31, wherein the degree of homogenization is calculated using a linear combination of attenuation values and/or functions of attenuation values, the parameters being coefficients in the linear combination.

* * * * *

UNITED STATES PATENT AND TRADEMARK OFFICE
CERTIFICATE OF CORRECTION

PATENT NO. : 5,343,044

DATED : August 30, 1994

INVENTOR(S) : J. SJAUNJA et al.

It is certified that error appears in the above-identified patent and that said Letters Patent is hereby corrected as shown below:

Column 3, line 63, delete "if" and insert --is--.

Claim 26:

Column 12, line 11, delete "on the concentration" and insert --on the degree of homogenization, and a relatively low dependency on the concentration".

Column 12, line 13, delete "a set a" and insert --a set of--.

Column 12, line 14, delete "known a known" and insert --a known--

Column 12, lines 14-15, delete "concentrations" and insert --concentration--.

Claim 35:

Column 12, line 63, delete "1" and insert --31--.

Signed and Sealed this

Fourth Day of April, 1995

*Attest:*

BRUCE LEHMAN

*Attesting Officer*     *Commissioner of Patents and Trademarks*